United States Patent [19]

Frump et al.

[11] 4,042,520
[45] Aug. 16, 1977

[54] THERMOGENIC SYSTEM

[75] Inventors: John Adams Frump; Jerry Hoyt Hunsucker, both of Terre Haute, Ind.

[73] Assignee: IMC Chemical Group, Inc., Terre Haute, Ind.

[21] Appl. No.: 655,321

[22] Filed: Feb. 5, 1976

[51] Int. Cl.² ............................ C09K 3/00; C09K 3/18; C09K 5/00
[52] U.S. Cl. ........................................ 252/70; 126/263; 252/90; 252/188.3 R; 260/307 F; 260/307 FA
[58] Field of Search ......... 252/90, 188.3, 70, 188.3 R; 424/45, 47, 73; 126/263; 260/307 F, 307 FA; 44/3, 3 R; 149/37, 119; 244/134 R

[56] References Cited

U.S. PATENT DOCUMENTS

| | | | |
|---|---|---|---|
| 2,261,221 | 11/1941 | Bruner | 126/263 |
| 3,281,310 | 10/1966 | Danielson | 260/307 FA |
| 3,461,073 | 8/1969 | Crowell, Jr. et al. | 252/70 |
| 3,535,246 | 10/1970 | Crowell, Jr. | 252/70 |
| 3,866,800 | 2/1975 | Schmitt | 252/188.3 |

FOREIGN PATENT DOCUMENTS 897,420   4/1972   Canada .................................... 44/3

OTHER PUBLICATIONS

Senkus, Some New Deriv. of Amino-Hydroxy cpds, Journal of Am. Chem. Soc. 67, pp. 1515-1519 (1945).

Bergman, The Oxazolidines vol. 53, 1953, Chemical Reviews, Williams & Wilkins, p. 321.

*Primary Examiner*—Harris A. Pitlick
*Attorney, Agent, or Firm*—Roger A. Williams; Howard E. Post

[57] ABSTRACT

A thermogenic system based on exothermic chemical reactions for heating consumer-type products as dispensed from suitable packages. The system includes the redox reactions of hydrogen peroxide as the oxidant and as the reductant compounds of the general oxazolidine formula

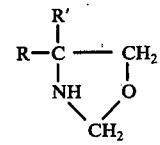

wherein R and R' may be the same or different and are selected from the group consisting of hydrogen, alkyl of from 1 to 4 carbon atoms, and substituted alkyl such as hydroxyalkyl e.g. hydroxymethyl. The effectiveness of the system can be enhanced by the addition of a catalyst selected from the group consisting of p-toluene sulfonic acid, iron filings, and iron salts of either the ferrous of ferric ions such as sulfates and halides thereof e.g. $FeSO_4$ and $FeCl_3$.

35 Claims, No Drawings

THERMOGENIC SYSTEM

BACKGROUND OF THE INVENTION

The present invention relates to a thermogenic system and more particularly, to means for generating heat in compositions dispensed from container packages.

There is a public need for dispensing means that will dispense warmed or hot compositions for shaving creams, shampoos, cleaning agents, disinfectants, deicers, and the like. Considerable effort has been directed to redox reactions of sulfur-containing organic compounds. Among the more recent thermogenic systems is that described by Moses et al., U.S. Pat. No. 3,341,418, wherein a redox reaction between hydrogen peroxide and thiourea or various thiobarbituric acid derivatives is disclosed. A disadvantage of this process, however is that for every mole of thiourea reacted, one mole of sulfuric acid is formed, necessitating the presence of excess alkali to prevent the destruction of soap in a soap-containing composition.

Another redox heating system is found in Antonelli et al., U.S. Pat. No. 3,632,516, which employs as a reductant, potassium thiosulfate and potassium sulfite with a sodium tungstate catalyst. While oxidation of thiosulfate ion provides a greater heat yield than does the oxidation of thiourea, the problem with the system is the fact that for every mole of thiosulfate oxidized, two moles of sulfate ion are generated requiring again the presence of excess base to prevent the pH from dropping so as to inhibit the formation of a soap. The thiosulfate and sulfite salts tend to cause gelling of soap compositions and are also highly corrosive to metal dispensing containers and to the valve means commonly utilized with such.

Another redox heating system is found in Margolis, U.S. Pat. No. 3,804,771, which employs as a reductant, xanthates, dithiocarbamates, and combinations of formaldehyde and molecular entities incorporating a

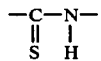

grouping using hydrogen peroxide as the oxidant. The problem with this system is that again sulfate ion is a reaction problem thus necessitating the use of excess alkali to prevent soap degradation. Free formaldehyde is present in the system and may be liberated. Since formaldehyde is a severe skin irritant it is necessary to add a bisulfite salt to the system when it is to be used in personal-care products. The liberation of free formaldehyde is temperature dependent. There is, therefore, an inherent defect in the system: when more heat is generated by the mixing, more free formaldehyde is liberated, thus requiring more bisulfite salt.

SUMMARY OF THE INVENTION

It is an object of this invention to provide a thermogenic system wherein sufficient heat is generated to produce a sensible rise in temperature.

Another object of this invention is to produce a thermogenic system for generating heat in compositions dispensed from container packages.

It is a further object of this invention to provide a thermogenic system wherein a selected temperature rise may be obtained by adjusting the concentrations of thermogen and hydrogen peroxide prior to mixing.

An additional object of this invention is to provide a thermogenic system for use in consumer-type products wherein said thermogenic system is compatible with the consumer-type product and the container in which the system is contained.

Other objects of this invention will be apparent to those skilled in the art from the disclosure herein.

A thermogenic system has now been found for generating heat consisting essentially of hydrogen peroxide in reaction with an oxazolidine thermogen having the general formula

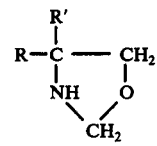

wherein R and R' may be the same or different and are selected from the group consisting of hydrogen, alkyl of from 1 to 4 carbon atoms and substituted alkyl such as hydroxyalkyl e.g. hydroxymethyl. The effectiveness of the system can be enhanced by the addition of a catalyst selected from the group consisting of p-toluene sulfonic acid, iron fillings and iron salts of either the ferrous or ferric ions such as sulfates and halides thereof e.g. FeSO$_4$ and FeCl$_3$.

Further the result of heat generation upon mixing H$_2$O$_2$ and the oxazolidine thermogen was unobvious and unexpected. When H$_2$O$_2$ was mixed with bicyclic oxazolidines no significant reaction occurred. However, when H$_2$O$_2$ was mixed with the monocyclic oxazolidines of the present invention the surprising and unexpected result was obtained that heat was generated and an exothermic reaction had occurred.

DETAILED DESCRIPTION OF THE INVENTION

It has been found that heat is generated when hydrogen peroxide is reacted with a compound of the general oxazolidine formula

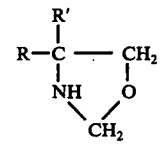

wherein R and R' may be the same or different and are selected from the group consisting of hydrogen, alkyl of from 1 to 4 carbon atoms, and substituted alkyl such as hydroxyalkyl, e.g. hydroxymethyl. This exothermic reaction occurring upon mixing can be enhanced by the addition of small amounts of a catalyst selected from the group consisting of p-toluene sulfonic acid, iron filings, or iron salts of either the ferrous or ferric ions such as sulfates and halides thereof e.g. FeSO$_4$ and FeCl$_3$. By varying the concentrations of the oxazolidine thermogen and/or hydrogen peroxide and with or without the addition of a catalyst any desired temperature rise can be effectuated in any composition in any amount of time. The rate of heat generation is dependent upon the concentrations of oxazolidine thermogen, hydrogen peroxide and upon wether a catalyst is present and if so which catalyst is present.

The catalysts employed in this invention can be any material that will affect the mixing of the oxazolidine thermogen and hydrogen peroxide to yield a faster or greater heat generation. Preferably the catalyst is selected from p-toluene sulfonic acid, iron fillings or iron salts of the ferrous or ferric ions such as the halides or sulfates thereof e.g. $FeSO_4$ and $FeCl_3$. Most preferable is the selection of p-toluene sulfonic acid as yielding the greatest heat generation per unit time per amount of catalyst. Preferably the amount of catalyst is from about 0.1 g to about 3 g per 0.1M of oxazolidine thermogen. Generally amounts less than 0.1 g do not significantly affect the rate of heat generation and amounts greater than 3 g do not significantly increase the effectiveness of the system.

The hydrogen peroxide used in the practice of this invention can vary in concentration depending upon the desired heat generation. Similarly, the concentration of oxazolidine thermogen can also vary depending on the desired heat generation and temperature rise sought. The concentrations can be varied either independently or in conjunction with each other to affect the rate of heat generation upon mixing. The maximum heat generation obtainable with the thermogenic system of the present invention is substantially the limits of solubility of any of the particular combinations. Preferably the oxazolidine thermogen and hydrogen peroxide are present in from 0.1 to 1 moles per 100 g of material to be heated having a heat capacity of about 1 cal/g. Generally amounts less than 0.1 moles do not significantly affect the rate of heat generation and amounts greater than 1 mole do not significantly increase the effectiveness of the system.

The oxazolidine thermogens of this invention are prepared by a condensation reaction, well-known within the art, in which the appropriate amino alcohol is condensed with formaldehyde to yield the desired oxazolidine. The reaction is discussed by Bergmann, *Chemical Reviews* 53 309–352 (1953).

The oxazolidines used as thermogens in the practice of this invention are prepared from amino alcohols in which the amine group and hydroxyl group are on adjacent carbon atoms. Some of the oxazolidine thermogens can be prepared from commercially available amino alcohols which include but are not limited to 2-amino-1-butanol, 2-amino-2-methyl-1-propanol, 2-amino-2-methyl-1,3-propanediol, and 2-amino-2-ethyl-1,3-propanediol. Other amino alcohols from which oxazolidine thermogens of this invention can be prepared, can themselves be prepared by reduction of nitroalcohols formed by condensation reactions of known nitroalkanes with formaldehyde. Some of these amino alcohols and the nitroalkanes from which they are derived include but are not limited to 2-amino-1-propanol from nitroethane, 2-amino-1,3-propanediol from nitromethane, 2-amino-1-pentanol and 2-amino-2-methyl-1-butanol from 1-nitrobutane and 2-nitrobutane respectively. Similarly the other oxazolidine thermogens of this invention can be prepared by the condensation reaction of the appropriate nitroalkane and formaldehyde to yield the nitroalcohol, reduction of the nitroalcohol to the aminoalcohol followed by another condensation reaction with formaldehyde to give the oxazolidine thermogen. These condensation and reduction reactions are well known in the art.

It is an embodiment of this invention to provide a heat generating combination of an oxazolidine thermogen and hydrogen peroxide. Upon mixing the oxazolidine thermogen and hydrogen peroxide heat is generated. In the practice of this invention it is therefore necessary to keep the components separated until the time for heat generation is needed and thereupon mixing the components. One method of accomplishing this is to provide a two compartment container. One compartment to contain the oxazolidine thermogen, the reductant, the other to contain the hydrogen peroxide oxidant. The two compartment container allows for the components to mix immediately before use, whereby upon mixing sufficient heat is evolved to produce a sensible rise in temperature of the dispensed mixture.

A sensible temperature rise is a noticeable temperature rise. A temperature rise of at least 25° C. above room temperature is generally considered desirable.

Any suitable two compartment container, many of which are known, can be employed for the practice of the present invention. Substances such as carriers, media, or propellants, if used, must be of such a nature that they do not interfere with the effectiveness of the dispensed ingredients and thus must be fully compatible therewith.

The thermogenic systems of the present invention can be used with compatible and conventional consumer-type ingredients or any other material to be heated. Preferably, the thermogenic system is separated into a two-part system within isolated compartments in a dispensing package. The thermogen being in one part and the hydrogen peroxide in the other. The thermogen may contain the consumer-type ingredient or material to be heated if compatible. It is to be understood that neither the material to be heated nor the consumer-type ingredients form a part of the present invention.

As above-mentioned, the thermogen and hydrogen peroxide are packaged within a container in such a way as to remain isolated from each other. Valve means are provided to connect with each of the compositions such that upon actuation of the valve means a quantity of each composition is brought together and dispensed from the package. The quantity and concentration of the materials must be adjusted in relation to the proportioning properties of the valve means to attain the desired temperature rise and product effect. This is simply a matter of choice and is dependent on the type of container means being utilized whether squeeze tube or aerosol container and product being dispensed.

The proportion of thermogen and hydrogen peroxide to the total composition depends upon how much heat is desired, how much heat is required to heat the composition itself, and the rate at which the heat is dissipated. Generally, a much higher temperature rise will be utilized with consumer-type ingredients that are not used for personal-care products. Temperature rises may be obtained wherein the dispensed product will be at or near the boiling point, ca. 100° C., but for personal-care type products maximum temperatures of about 70° C. are sufficient.

It is another embodiment of the present invention to provide a method of heating a material by combining therewith sequentially an oxazolidine thermogen and hydrogen peroxide in amounts sufficient to produce a sensible temperature rise in the total composition.

Preparative examples showing the thermogenic properties and uses for the thermogenic system of the present invention in various consumer products are shown, and which are intended solely to illustrate the invention and not to limit it. In the specific examples given hereinbelow, the weight ratio of oxazolidine reductant mixture to oxidant is about 3:1. It is to be understood that this ratio may be widely varied to produce an effective product and can range from about 10:1 to 1:10 depending on the valve means used, thermogen and oxidant reacted, the reactant concentrations, the temperature rise desired, and the type of product being dispensed.

EXAMPLE 1

Twelve grams (0.114 moles) of 4,4-dimethyl-1,3-oxazolidine in 13 g of water was added to 3.9 g (0.114 moles) of hydrogen peroxide (100% basis) in 71.1 g water. There was a slow rise in temperature finally increasing from 30° to 78° C in 10 minutes. In another run 23 g (0.227 moles) of 4,4-dimethyl-1,3-oxazolidine in 52 g of water was added to 7.8 g (0.227 moles) hydrogen peroxide (100% basis) in 18.2 g water. The temperature rise was more rapid, from 30° C to 80° C in 90 sec. and the mixture was boiling at 100 sec. In still another run 23 g (0.227 moles) of 4,4-dimethyl-1,3-oxazolidine in 2 g water was added to 7.8 g (0.227 moles) hydrogen peroxide (100% basis) in 67.2 g water and the temperature rise observed was even more rapid, reaching the boiling point, 100° C, in 80 seconds. In all three of the above runs a total of 100 g of materials was used. The final concentration of hydrogen peroxide was 3.9% and the 4,4-dimethyl-1,3-oxazolidine final concentration was 12% in the first run. The final concentrations of the resultant mixtures in the last two runs were identical, each containing 7.8% of hydrogen peroxide and 23% 4,4-dimethyl-1,3-oxazolidine. The only difference in these last two runs was in the concentrations of the individual components prior to mixing.

A hot shaving cream employing the thermogenic system of this invention is prepared in a two-compartment package according to the following formula:

| Mixture I | Parts by Weight |
| --- | --- |
| Stearic Acid | 6.23 |
| Coconut oil fatty acids | 1.39 |
| Mineral oil | 1.00 |
| Water, about | 65.00 |
| Heat to 70° C to mix | |
| Cool to 40° C and add with stirring: | |
| 4,4-Dimethyl-1,3-oxazolidine | 17.5 |
| Perfume | 0.8 |
| Water to make | 100.0 |
| Mixture II | Parts by Weight |
| Hydrogen peroxide (50%) | 25 |
| Purified water to make | 100 |

Mixture I is placed in an aerosol can and pressurized with a fluorocarbon propellant mixture of dichlorodifluoromethane with dichlorofluoroethane in a weight ratio of 40/60. A co-dispensing valve to which is attached to flexible container, is crimped into the can opening. The flexible container is filled with Mixture II (the valve being designed to meter out about 3 parts of Mixture I and 1 part of Mixture II). On being actuated, the valve dispenses a rich lather which begins warming up as it is dispensed.

EXAMPLE 2

The experiment of Example 1 is repeated in all essential details except that 4-ethyl-1,3oxazolidine prepared by condensing 2-amino-1-butanol with formaldehyde is substituted for 4,4-dimethyl-1,3-oxazolidine.

The thermogenic system of this invention is employed to create a hot cleansing cream in a two-compartment package according to the following formula:

| Mixture I | Parts by Weight |
| --- | --- |
| Mineral oil | 30.0 |
| Lanolin | 1.0 |
| Cetyl alcohol | 1.0 |
| Water | 33.0 |
| Heat to about 70° C and mix. | |
| Cool to about 40° C and add: | |
| 4-Ethyl-1,3-oxazolidine | 34.0 |
| Perfume | 0.8 |
| Water to make | 100.0 |
| Mixture II | |
| Hydrogen peroxide, 50% | 25 |
| Purified water to make | 100 |

Mixture I is placed in an aerosol can, pressurized with a fluorocarbon propellant mixture of dichlorodifluoromethane with dichlorofluoroethane in a weight ratio of 40/60. A co-dispensing valve, to which is attached a flexible container filled with Mixture II (the valve being designed to meter about 3 parts Mixture I and 1 part Mixture II) is crimped into the opening of the can. On being activated, the valve dispenses a rich lather which begins warming up as it is dispensed and breaks down to a creamy consistency as it is rubbed over the skin.

EXAMPLE 3

The experiment of Example 1 is repeated in all essential details except that 4-hydroxymethyl-4-methyl-1,3-oxazolidine is substituted for 4,4-dimethyl-1,3-oxazolidine. 4-Hydroxymethyl-4-methyl-1,3-oxazolidine is prepared from the condensation reaction of 2-amino-2-methyl-1,3-propanediol with formaldehyde. A similar rise in temperature is observed when 4-hydroxymethyl-4-methyl-1,3-oxazolidine is mixed with hydrogen peroxide.

EXAMPLE 4

The experiment of Example 1 is repeated in all essential details except that 4-propyl-1,3-oxazolidine, prepared by condensing 2-amino-1-pentanol with formaldehyde, is substituted for 4,4-dimethyl-1,3-oxazolidine. 4-Propyl-1,3-oxazolidine is mixed with hydrogen peroxide and a similar rise in temperature occurs.

EXAMPLE 5

The experiment of Example 1 is repeated in all essential details with the exception that 4-butyl-1,3-oxazolidine, prepared by condensing 2-amino-1-hexanol with formaldehyde, is substituted for 4,4-dimethyl-1,3-oxazolidine. 4-Butyl-1,3-oxazolidine is mixed with hydrogen peroxide and a similar temperature rise is observed.

The above Examples 1–5 indicate the utility of the thermogenic system of the present invention when an oxazolidine thermogen is mixed with hydrogen peroxide. The following examples illustrates the effect on that thermogenic system when a catalyst is added. Preferably the catalysts employed in this invention are present from about 0.1 g to about 3 g for 100 g of material to be heated having a heat capacity of 1 cal/g.

EXAMPLES 6–9

The following examples were conducted to determine the effect of catalysts on the thermogenic system wherein 4,4-dimethyl-1,3-oxazolidine and hydrogen peroxide were mixed. The concentrations of oxazolidine thermogen, hydrogen peroxide, and catalyst and the results of each run per example are given in the Table. The various runs were conducted by mixing in sequence the oxazolidine thermogen, the catalyst, and the hydrogen peroxide.

TABLE

| Ex. No. | 4,4-Dimethyl-1,3-oxazolidine | 30% $H_2O_2$ | ml. $H_2O$ | Catalyst | Temp. Rise, °C | Time Min. |
|---|---|---|---|---|---|---|
| 6 | 12 g | 7.8 g | 100 | 0 | 24 – 58 | 13 |
|   | 12 g | 7.8 g | 100 | .5 g Iron Filings | 25 – 60 | 9 |
|   | 12 g | 7.8 g | 100 | 1.0 g Iron Filings | 25 – 60 | 6.5 |
|   | 12 g | 7.8 g | 100 | 1.5 g Iron Filings | 25 – 59 | 6 |
| 7 | 12 g | 7.8 g | 100 | 1.0 g $FeSO_4 \cdot 7H_2O$ | 25 – 52 | 3.5 |
| 8 | 12 g | 7.8 g | 100 | 1.0 g $FeCl_3 \cdot 6H_2O$ | 25 – 50 | 2 |
|   | 12 g | 7.8 g | 100 | 2.0 g $FeCl_3 \cdot 6H_2O$ | 25 – 49 | 2 |
| 9 | 12 g | 7.8 g | 100 | 1.0 p-Toluene sulfonic acid | 25 – 63 | 5 |
|   | 36 g | 7.8 g | 56.2 | 1.0 g p-Toluene sulfonic acid | 25 – 78 | 2½ |
|   | 36 g | 7.8 g | 56.2 | 0 | 26 – 60 | 2½ |

A hot antiseptic hand cleaner is prepared using the thermogenic system of this invention in a two-compartment package:

| Mixture I | Parts by Weight |
|---|---|
| Tincture of greensoap | 74.5 |
| 4,4-dimethyl-1,3-oxazolidine | 22.2 |
| P-toluene-sulfonic acid | 1.0 |
| Hexachlorophene | 2.0 |
| Perfume | 0.3 |
| Mixture II | |
| Hydrogen peroxide, 50% | 25 |
| Purified water to make | 100 |

Mixture I is placed in an aerosol can, pressurized with a fluorocarbon propellant mixture of dichlorodifluoromethane with dichlorofluoroethane in a weight ratio of 40/60. A co-dispensing valve, to which is attached a flexible container filled with Mixture II (the valve being designed to meter about 3 parts of Mixture I and 1 part of Mixture II) is crimped into the opening of the can. On being actuated, the valve dispenses a rich lather, which begins warming up as it is dispensed.

EXAMPLE 10

| Mixture I | Parts by Weight |
|---|---|
| Water | 15.4 |
| Ethylene glycol | 10.0 |
| Isopropanol | 60.0 |
| 4-Hydroxymethyl-4-methyl-1,3-oxazolidine | 13.6 |
| $FeCl_3 \cdot 6H_2O$ | 1.0 |
| Mixture II | Parts by Weight |
| Hydrogen peroxide, 50% | 50 |
| Purified water | 50 |

When sprayed from a co-dispensing aerosol can onto the ice-covered windshield of an automobile in the proportion of about 3 parts Mixture I to about 1 part Mixture II, sufficient heat is generated in several seconds, to melt the ice rapidly.

The above examples illustrate that the present invention of a thermogenic system possesses the ability to be selectively varied to meet the specifications of the desired consumer-type product. The amount of heat generated in any unit time may be selectively controlled by varying the concentrations of oxazolidine thermogens and/or hydrogen peroxide and/or by the addition of one of the abovenamed catalysts. The maximum temperature rise obtainable with the thermogenic system of the present invention is substantially the limits of solubility of any of the particular combinations.

We claim:

1. A thermogenic system for generating heat comprising hydrogen peroxide in reaction with an oxazolidine thermogen having the general formula

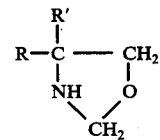

wherein R and R' may be the same or different and are selected from the group consisting of hydrogen, alkyl of from 1 to 4 carbon atoms, and hydroxymethyl in an effective amount sufficient to produce a sensible temperature rise.

2. The thermogenic system of claim 1 wherein said thermogen is 4,4-dimethyl-1,3-oxazolidine.

3. The thermogenic system of claim 1 wherein said thermogen is 4-ethyl-1,3-oxazolidine.

4. The thermogenic system of claim 1 wherein said thermogen is 4-hydroxymethyl-4-methyl-1,3-oxazolidine.

5. The thermogenic system of claim 1 wherein said thermogen is 4-propyl-1,3-oxazolidine.

6. The thermogenic system of claim 1 wherein said thermogen is 4-butyl-1,3-oxazolidine.

7. The thermogenic system of claim 1 wherein said thermogen is present in an amount sufficient to produce at least about a 25° C temperature rise when reacted with said hydrogen peroxide.

8. The thermogenic system of claim 1 wherein is added a sufficient amount of catalyst selected from the group consisting of p-toluene sulfonic acid, iron filings, and iron salts.

9. The thermogenic system of claim 8 wherein said thermogen is 4,4-dimethyl-1,3-oxazolidine and said catalyst is p-toluene sulfonic acid.

10. The thermogenic system of claim 8 wherein said thermogen is 4,4-dimethyl-1,3-oxazolidine and said catalyst is iron filings.

11. The thermogenic system of claim 8 wherein said thermogen is 4,4-dimethyl-1,3-oxazolidine and said catalyst is $FeCl_3$.

12. The thermogenic system of claim 8 wherein said thermogen is 4,4-dimethyl-1,3-oxazolidine and said catalyst is $FeSO_4$.

13. The thermogenic system of claim 8 wherein said thermogen is 4-ethyl-1,3-oxazolidine and said catalyst is p-toluene sulfonic acid.

14. The thermogenic system of claim 8 wherein said thermogen is 4-hydroxymethyl-4-methyl-1,3-oxazolidine and said catalyst is p-toluene sulfonic acid.

15. The thermogenic system of claim 8 wherein said thermogen, hydrogen peroxide, and catalyst are present in amounts sufficient to produce at least about a 25° C temperature rise.

16. A two part thermogenic system arranged in a dispensing package with consumer-type compositions, the parts to be mixed at the time of dispensing from the package in relative amounts sufficient to effect a sensible temperature rise in the dispensed mixture; comprising one part consisting essentially of hydrogen peroxide; said other part consisting of the consumer-type composition and a thermogen having the general formula

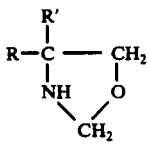

wherein R and R' may be the same or different and are selected from the group consisting of hydrogen, alkyl of from 1 to 4 carbon atoms, and hydroxymethyl.

17. The two part thermogenic system of claim 16 wherein said thermogen is 4,4-dimethyl-1,3-oxazolidine.

18. The two part thermogenic system of claim 16 wherein said thermogen is 4-ethyl-1,3-oxazolidine.

19. The two part thermogenic system of claim 16 wherein said thermogen is 4-hydroxymethyl-4-methyl-1,3-oxazolidine.

20. The two part thermogenic system of claim 16 wherein said thermogen and hydrogen peroxide are present in an amount sufficient to produce at least about a 25° C temperature rise when mixed.

21. The two part thermogenic system of claim 16 wherein is added a catalyst selected from the group consisting of p-toluene sulfonic acid, iron filings and iron salts.

22. The two part thermogenic system of claim 16 wherein said thermogen is 4,4-dimethyl-1,3-oxazolidine and said catalyst is p-toluene sulfonic acid.

23. A method of heating a material selected from shaving cream, cleansing cream, hand cleanser and windshield de-icer comprising the steps of
 a. combining with the material to be heated an oxazolidine thermogen of the general formula

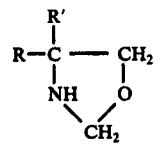

wherein R and R' may be the same or different and are selected from the group consisting of hydrogen, alkyl of from 1 to 4 carbon atoms, and hydroxymethyl, and
 b. mixing therewith hydrogen peroxide, in an amount sufficient to produce a sensible temperature rise in the mixture.

24. The method of claim 23 wherein said thermogen is 4,4-dimethyl-1,3-oxazolidine.

25. The method of claim 23 wherein said thermogen is 4-ethyl-1,3-oxazolidine.

26. The method of claim 23 wherein said thermogen is 4-hydroxymethyl-4-methyl-1,3-oxazolidine.

27. The method of claim 23 wherein is added the additional step of adding a catalyst selected from the group consisting of p-toluene sulfonic acid, iron filings, and iron salts to the oxazolidine thermogen and material to be heated mixture, and prior to the mixing of hydrogen peroxide.

28. The method of claim 27 wherein said catalyst is p-toluene sulfonic acid.

29. The method of claim 28 wherein said thermogen is 4,4-dimethyl-1,3-oxazolidine.

30. The method of claim 27 wherein said catalyst is iron filings.

31. The method of claim 30 wherein said thermogen is 4,4-dimethyl-1,3-oxazolidine.

32. The method of claim 27 wherein said catalyst is $FeSO_4$.

33. The method of claim 32 wherein said thermogen is 4,4-dimethyl-1,3-oxazolidine.

34. The method of claim 27 wherein said catalyst is $FeCl_3$.

35. The method of claim 34 wherein said thermogen is 4,4-dimethyl-1,3-oxazolidine.

* * * * *

UNITED STATES PATENT AND TRADEMARK OFFICE
CERTIFICATE OF CORRECTION

PATENT NO. : 4,042,520
DATED : August 16, 1977
INVENTOR(S) : J. A. Frump and J. H. Hunsucker It is certified that error appears in the above-identified patent and that said Letters Patent are hereby corrected as shown below:

In the Abstract, third line from the bottom, after "ferrous" delete "of" and substitute therefor --or--

Column 1, line 47, "problem" should read --product--

Column 1, line 62, "produce" should read --provide--

Column 2, line 26, "fillings" should read --filings--

Column 2, line 67, "wether" should read --whether--

Column 3, line 5, "fillings" should read --filings--

Column 5, line 54, delete the word "to" and substitute therefor --a--

Column 7, line 38, after "Example 10" insert --Hot Windshield De-Icer--

Signed and Sealed this

Twentieth Day of December 1977

[SEAL]

Attest:

RUTH C. MASON
Attesting Officer

LUTRELLE F. PARKER
Acting Commissioner of Patents and Trademarks